United States Patent
Lee et al.

(10) Patent No.: US 12,263,470 B2
(45) Date of Patent: Apr. 1, 2025

(54) METHOD OF IMPROVING SELECTIVE HYDROGENATION OF UNSATURATED HYDROCARBON IN AROMATIC FRACTION THROUGH CATALYST PRETREATMENT

(71) Applicants: SK Innovation Co., Ltd., Seoul (KR); SK Geo Centric Co., Ltd., Seoul (KR)

(72) Inventors: Sang Il Lee, Daejeon (KR); Ji Hoon Lee, Daejeon (KR)

(73) Assignees: SK Innovation Co., Ltd., Seoul (KR); SK Geo Centric Co., Ltd., Seoul (KR)

( * ) Notice: Subject to any disclaimer, the term of this patent is extended or adjusted under 35 U.S.C. 154(b) by 0 days.

(21) Appl. No.: 18/669,691

(22) Filed: May 21, 2024

(65) Prior Publication Data

US 2024/0299912 A1    Sep. 12, 2024

Related U.S. Application Data

(62) Division of application No. 17/973,669, filed on Oct. 26, 2022, now Pat. No. 12,011,709.

(30) Foreign Application Priority Data

Oct. 27, 2021    (KR) .................. 10-2021-0144230

(51) Int. Cl.

| | | |
|---|---|---|
| *B01J 21/04* | (2006.01) | |
| *B01J 23/755* | (2006.01) | |
| *B01J 23/882* | (2006.01) | |
| *B01J 23/883* | (2006.01) | |
| *B01J 35/30* | (2024.01) | |
| *B01J 37/14* | (2006.01) | |
| *B01J 37/18* | (2006.01) | |
| *B01J 37/20* | (2006.01) | |
| *C07C 5/11* | (2006.01) | |
| *C07C 5/27* | (2006.01) | |
| *C07C 6/06* | (2006.01) | |

(52) U.S. Cl.
CPC ............. *B01J 23/883* (2013.01); *B01J 21/04* (2013.01); *B01J 23/755* (2013.01); *B01J 23/882* (2013.01); *B01J 35/394* (2024.01); *B01J 37/14* (2013.01); *B01J 37/18* (2013.01); *B01J 37/20* (2013.01); *C07C 5/11* (2013.01); *C07C 5/2735* (2013.01); *C07C 5/2754* (2013.01); *C07C 6/06* (2013.01); *C07C 2521/04* (2013.01); *C07C 2523/755* (2013.01); *C07C 2523/882* (2013.01); *C07C 2523/883* (2013.01)

(58) Field of Classification Search
CPC ........ B01J 23/883; B01J 21/04; B01J 23/755; B01J 23/882; B01J 35/394; B01J 37/14; B01J 37/18; B01J 37/20; B01J 23/002; B01J 37/0205; B01J 37/088; B01J 27/0515; B01J 37/02; B01J 37/08; B01J 37/12; B01J 37/16; C07C 5/11; C07C 5/2735; C07C 5/2754; C07C 6/06; C07C 2521/04; C07C 2523/755; C07C 2523/882; C07C 2523/883; C07C 7/163; C07C 2/74; C07C 15/08; Y02P 20/52; C10G 45/38

See application file for complete search history.

(56) References Cited

U.S. PATENT DOCUMENTS

| | | |
|---|---|---|
| 3,114,701 A | 12/1963 | Jacobson et al. |
| 3,865,716 A | 2/1975 | Sosnowski |
| 2002/0002315 A1 | 1/2002 | Kelly et al. |
| 2007/0170098 A1 | 7/2007 | Bouchy et al. |

FOREIGN PATENT DOCUMENTS

KR    20130099017 A * 9/2013

OTHER PUBLICATIONS

English Translation of KR 20130099017 A (Year: 2013); Fabrice at al.*

* cited by examiner

*Primary Examiner* — Thuan D Dang
(74) *Attorney, Agent, or Firm* — The Webb Law Firm

(57) ABSTRACT

Disclosed is a method for providing improved hydrogenation activity by pretreating a catalyst in a three-step manner before selective hydrogenation of unsaturated hydrocarbons in an aromatic fraction in the presence of an oxide-type bimetallic (particularly nickel-molybdenum) supported catalyst.

20 Claims, 2 Drawing Sheets

METHOD OF IMPROVING SELECTIVE HYDROGENATION OF UNSATURATED HYDROCARBON IN AROMATIC FRACTION THROUGH CATALYST PRETREATMENT

CROSS REFERENCE TO RELATED APPLICATIONS

This application is a divisional of U.S. patent application Ser. No. 17/973,669, filed Oct. 26, 2022, which claims priority to Korean Patent Application No. 10-2021-0144230, filed Oct. 27, 2021, the disclosures of which are hereby incorporated in their entirety.

BACKGROUND OF THE INVENTION

Field of the Invention

The present disclosure relates to a method of improving the selective hydrogenation of unsaturated hydrocarbons in an aromatic fraction through catalyst pretreatment. More particularly, the present disclosure relates to a method for providing improved hydrogenation activity by pretreating a catalyst in a three-step manner before selective hydrogenation of unsaturated hydrocarbons in an aromatic fraction in the presence of a bimetallic (particularly nickel-molybdenum) supported catalyst.

Description of the Related Art

C6+ aromatic hydrocarbons, particularly benzene, toluene, or mixed xylene (or xylene isomers), account for a large proportion of sources of basic petrochemicals. Benzene or toluene is mainly used for solvents, fibers, disinfectants, pesticides, pharmaceutical intermediates, dyes, pigments, and the like. Mixed xylene typically includes meta-xylene (m-xylene), para-xylene (p-xylene), and ortho-xylene (o-xylene). Of these, p-xylene is a raw material used for synthesizing terephthalic acid used in the preparation of synthetic textile fibers and resins, and o-xylene is used as a raw material for preparing phthalic anhydride. Also, m-xylene is used for plasticizers, azo dyes, and the like. Since xylene isomers have similar boiling points to each other, it is difficult to separate a specific isomer from mixed xylene through a typical distillation method, so a method for separation and recovery using adsorptive separation, crystallization, isomerization, etc. is mainly applied.

As a commercial technique for producing benzene, toluene, or mixed xylene, separation and recovery methods from aromatic-rich fractions and chemical synthesis methods are generally known.

Among the methods noted above, the representative separation and recovery methods include distillation/separation of reformate produced through the catalytic reforming of naphtha, separation from pyrolysis oil obtained as a byproduct during naphtha pyrolysis, and the like.

Recently, since the affordable amount of xylene from the catalytic reforming is limited, there is growing interest in reactions to produce C8 aromatic hydrocarbons from aromatic hydrocarbons having a single benzene ring (aromatic hydrocarbons including benzene, toluene, and/or C9+ aromatics) using a zeolite-based catalyst.

However, aromatic hydrocarbon fractions such as catalytic reformate and pyrolysis oil contain small amounts of unsaturated hydrocarbons (e.g. olefins, acetylene, and/or alkenylbenzene (styrene, etc. or derivatives thereof)). Such unsaturated hydrocarbons deteriorate the performance of the adsorptive separation process for separating products, or are difficult to separate only through distillation as a typical separation technique, which decreases the purity of the products.

In order to solve the above problems, there is a known technique for decreasing the unsaturated hydrocarbon content in the feedstock of the downstream process by performing pretreatment such as clay treatment or hydrogenation.

In the clay treatment, unsaturated hydrocarbons may be dimerized or trimerized using clay having acid characteristics as an alkylation catalyst, or may be alkylated with aromatic hydrocarbons to thus form heavy aromatics, thereby removing the same as high-boiling-point fractions that are easy to separate, and processes based thereon have been widely commercialized. However, clays are deactivated within a relatively short time during the process of removing unsaturated hydrocarbons from the aromatic fraction, and thus problems, such as processing inefficiency and increased costs due to frequent clay replacement, and solid waste generation, may occur.

Moreover, light aromatics such as benzene, toluene, xylene, and the like, which should be recovered as targeted products, are converted into heavy aromatics by alkylation with unsaturated hydrocarbons, causing loss of aromatic products, which is undesirable.

On the other hand, as for the hydrogenation method, unsaturated hydrocarbons (i.e. olefins, acetylene, and/or alkenylbenzene (styrene, etc. or derivatives thereof)) in the aromatic fraction are removed in a manner of being converted into saturated hydrocarbons (i.e., paraffins) or ethylbenzene (including derivatives thereof) by supplying hydrogen in the presence of a catalyst, which may solve problems associated with the clay treatment such as frequent clay replacement, and may reduce the cost of clay, generation of waste, and loss of light aromatics.

Recently, processes for removing unsaturated hydrocarbons from aromatic fractions have been commercialized by major companies; for example, Olefin Reduction Unit (ORU) technology from UOP, Olgone™ technology from Exxon-Mobil and Arofining technology from Axens are known. In particular, for selective hydrogenation, nickel-based catalysts, noble-metal-based catalysts (Pt, Pd, etc.), cobalt-molybdenum (Co—Mo) catalysts, nickel-molybdenum (Ni—Mo) catalysts, etc. known in the art are used as typical hydrogenation catalysts.

Although it is required to selectively saturate only unsaturated hydrocarbons (e.g. having at least one double-bonded hydrocarbon or triple-bonded hydrocarbon) while minimizing aromatic loss during the hydrogenation, each of the catalysts described above causes high degree of aromatic loss (not only unsaturated hydrocarbons but also aromatic rings are saturated), or has good removal efficiency of unsaturated hydrocarbons but low durability (ability to maintain catalytic activity upon long-term operation). In particular, the Ni—Mo-based catalyst (especially a reduced type thereof) widely used as a hydrogenation catalyst has high hydrogenation activity for unsaturated hydrocarbons such as olefins, acetylene, and/or alkenylbenzene compared to other hydrogenation catalysts, such as Co—Mo-based catalysts, but tends to increase aromatic loss due to hydrogenation of the benzene ring. Accordingly, there is need for catalyst technologies capable of exhibiting high hydrogenation activity for unsaturated hydrocarbons in the aromatic fraction and simultaneously suppressing aromatic loss.

SUMMARY OF THE INVENTION

An embodiment of the present disclosure is intended to provide a catalyst system capable of removing unsaturated hydrocarbons from an aromatic hydrocarbon fraction through selective hydrogenation, while suppressing aromatic loss, and maintaining good hydrogenation activity even upon long-term operation.

A first aspect of the present disclosure provides a method for preparing a selective hydrogenation catalyst for an unsaturated hydrocarbon in an aromatic fraction, which comprises the steps of:
step a) providing a catalyst containing nickel and molybdenum;
step b) sulfiding the catalyst containing nickel and molybdenum to give a sulfided catalyst containing nickel and molybdenum;
step c) carrying out an oxidation treatment of the sulfided catalyst containing nickel and molybdenum at a temperature exceeding 250° C. to give an oxidized catalyst containing nickel and molybdenum; and
step d) carrying out a reduction treatment of the oxidized catalyst containing nickel and molybdenum to give a reduced catalyst containing nickel and molybdenum.

A second aspect of the present disclosure provides a method for removing unsaturated hydrocarbons from aromatic hydrocarbons, which comprises the steps of:
providing an aromatic hydrocarbon-containing having a bromine index of at least 30; and feedstock
forming an aromatic hydrocarbon-containing product having a decreased bromine index compared to the feedstock by hydrogenating the aromatic hydrocarbon-containing feedstock in the presence of a selective hydrogenation catalyst prepared using the method described above.

According to an exemplary embodiment, at least 30 wt % of the unsaturated hydrocarbons may be removed from the aromatic-hydrocarbon-containing feedstock.

According to an exemplary embodiment, aromatic loss upon production of the aromatic hydrocarbon-containing product from the aromatic hydrocarbon-containing feedstock may be less than 1 wt %.

BRIEF DESCRIPTION OF THE DRAWINGS

The above and other objects, features, and other advantages of the present invention will be more clearly understood from the following detailed description taken in conjunction with the accompanying drawings, in which.

DESCRIPTION OF THE INVENTION

Figure 1:
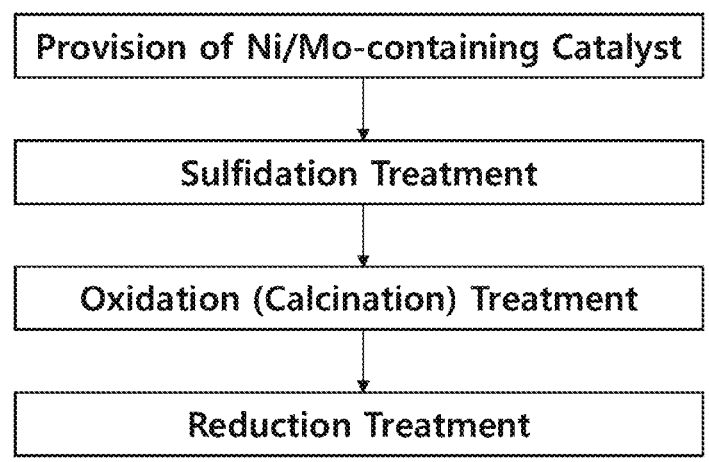
FIG. 1 shows the sequence of a three-step pretreatment process performed on a nickel-molybdenum catalyst according to an exemplary embodiment.

The present invention can be worked in its entirety based on the following description. It should be understood that the following description is given of preferred embodiments of the present invention, and the present invention is not necessarily limited thereto. In addition, the accompanying drawings are provided to aid understanding of the present invention, and the present invention is not limited thereto.

Terms used herein may be defined as follows. As used herein, the term "heterogeneous catalyst" refers to a catalyst that is present in a different phase from a reactant in a catalytic reaction. For example, a heterogeneous catalyst may remain undissolved in a reaction medium. When a heterogeneous catalyst is used, the reaction begins with the diffusion and adsorption of reactants onto the surface of the heterogeneous catalyst. After completion of the reaction, the product needs to be desorbed from the surface of the heterogeneous catalyst.

As used herein, the term "support" refers to a material (typically a solid-phase material) having a large specific surface area, onto which a catalytically active component is attached or deposited, and the support may or may not be involved in a catalytic reaction.

As used herein, the term "olefins" may be intended to include alkenes, cycloalkenes, alkenyl benzenes and the like.

As used herein, the term "disproportionation" refers to the transfer of alkyl radical from one molecule to the other in order to form two different products between same kind of molecules. For example, disproportionation of toluene may result in the production of benzene and xylene.

In a narrow sense, the term "transalkylation" refers to a reaction in which at least one alkyl radical (e.g., methyl, ethyl, propyl, butyl, or the like) is transferred from an organic compound to another.

As used herein, the term "dealkylation" refers to a reaction in which at least one alkyl group (e.g., methyl, ethyl, propyl, butyl, or the like) is eliminated from a hydrocarbon compound (specifically, an aromatic compound).

The term "xylene isomerization" may refer to an isomerization reaction that converts C8 aromatic hydrocarbons, particularly o-xylene and/or m-xylene, into p-xylene.

As used herein, the term "xylene isomerization" refers to isomerization of converting C8 aromatic hydrocarbons, more specifically ortho-xylene and/or meta-xylene, to para-xylene.

As used herein, the term "Cn+ aromatic" refers to an aromatic hydrocarbon having Cn or more carbon atoms, and similarly, the term "Cn-aromatic" refers to an aromatic hydrocarbon having Cn or fewer carbon atoms.

As used herein, the term "Cn+ hydrocarbon" refers to a hydrocarbon having Cn or more carbon atoms, and similarly, the term "Cn-hydrocarbon" refers to a hydrocarbon having Cn or fewer carbon atoms.

As used herein, the term "C8 aromatics" refers to aromatic hydrocarbons including mixed xylene (ortho-xylene, meta-xylene and para-xylene) and/or ethylbenzene.

As used herein, the term "bromine index (BI)" refers to a measured value (mg) of bromine consumed by 100 g of a hydrocarbon or hydrocarbon mixture, and may be used to indicate the percentage of unsaturated bonds present in the hydrocarbon. The bromine index may be measured, for example, according to ASTM D 2710-92.

As used herein, the term "rich" means that a particular compound is present, for example, in an amount of at least about 50%, specifically at least 70%, more specifically at least about 80%, particularly specifically, at least about 90%, on a predetermined basis (e.g., on a weight, volume or molar basis), in a fraction or a stream.

As used herein, the term "separation" may encompass physical and chemical separation in a broad sense, and may be understood to mean physical separation in a narrow sense.

Unless otherwise stated herein, it may be understood that the aromatic (or benzene) ring itself is excluded from the range of unsaturated hydrocarbons that are removed through selective hydrogenation, even though it contains a double bond therein.

According to an embodiment of the present disclosure, a catalyst containing nickel and molybdenum (e.g., a nickel-molybdenum (Ni—Mo) catalyst) is pretreated through a three-step process, whereby good selective hydrogenation activity for unsaturated hydrocarbons (particularly olefins, acetylene, and/or alkenylbenzene (such as styrene, etc. or derivatives thereof)) present in small amounts in an aromatic fraction (e.g. an alkyl aromatic fraction) may be exhibited, while aromatic loss (particularly, loss of benzene rings in aromatics) may be minimized.

Nickel-Molybdenum Catalyst

In an embodiment, the nickel-molybdenum (Ni—Mo) catalyst may be typically a heterogeneous catalyst in which Ni and Mo are supported on an inorganic support. Here, the catalyst may be in the form of a powder or a structure having a predetermined shape.

According to an exemplary embodiment, the inorganic support may be selected from among inorganic-oxide-based porous supports having a large specific surface area. For example, the inorganic support may be at least one selected from the group consisting of alumina, silica, silica-alumina, aluminum phosphate, zirconia, titania, bentonite, kaolin, clinoptilolite, and montmorillonite. According to a specific embodiment, the inorganic support may be amorphous, and may particularly be at least one selected from the group consisting of alumina, silica, and silica-alumina, more particularly alumina and/or silica, and still more particularly, alumina may be used.

According to an exemplary embodiment, the support in the form of a predetermined structure may be in a shaped or molded form, particularly a cylindrical form, having a diameter of about 0.5 to 5 mm (particularly about 1 to 3 mm) and a dimension of about 3 to 20 mm (particularly about 5 to 15 mm). Alternatively, the support may have a trilobe shape, a quadrilobe shape, a granular shape, a pellet shape, a tablet shape, a spherical shape, etc., in addition to the cylindrical shape. As such, for illustrative purposes, in order to prepare a support having a specific shape, any typical molding techniques known in the art, for example extrusion, spray drying, pelletizing, oil dropping, etc. may be performed.

According to an exemplary embodiment, the support may have an apparent density in the range of about 0.3 to 1.2 g/cc, particularly about 0.4 to 1.1 g/cc, and more particularly about 0.4 to 0.9 g/cc. Also, the average pore diameter of the support may be in the range of, for example, about 3 to 1000 nm, particularly about 5 to 800 nm, and more particularly about 7 to 600 nm. In addition, the specific surface area (BET) of the support may be in the range of, for example, about 10 to 1000 m$^2$/g, particularly about 30 to 800 m$^2$/g, and more particularly about 50 to 600 m$^2$/g. However, the numerical ranges for the properties described above are set forth merely for illustrative purposes.

In an exemplary embodiment, the amount of nickel in the catalyst may be set within the range of, for example, about 1 to 30 wt %, particularly about 2 to 20 wt %, and more particularly about 3 to 6 wt %, based on the total weight of the catalyst. Further, the amount of molybdenum in the catalyst may be set within the range of, for example, about 2 to 40 wt %, particularly about 5 to 25 wt %, and more particularly about 10 to 20 wt %, based on the total weight of the catalyst. The total amount of nickel and molybdenum may be in the range of, for example, about 3 to 50 wt %, particularly about 7 to 35 wt %, and more particularly about 10 to 30 wt %, based on the total weight of the catalyst. The amount ranges for the individual metals and total metal are set forth merely for illustrative purposes. However, if the amount of each of nickel and molybdenum is excessively low or high, the hydrogenation activity for unsaturated hydrocarbons may be insufficient, or side-reaction phenomena such as hydrogenation of the aromatic ring (i.e. the benzene ring) may be induced. Hence, it may be advantageous to appropriately adjust the amounts thereof within the above ranges.

According to an exemplary embodiment, in the Ni—Mo supported catalyst, the atomic ratio of nickel to molybdenum may be adjusted within the range of, for example, 1:about 0.1 to 10, particularly 1:about 0.5 to 5, and more particularly 1:about 1 to 3.

According to an exemplary embodiment, supporting Ni and Mo as active metals on an inorganic support may be performed through any techniques known in the art, for example, impregnation (e.g. incipient wetness impregnation, supersaturation impregnation, and immersion), ion-exchange, co-precipitation, and the like. Typically, the impregnation may be applied, where a soluble metal precursor or compound (typically a water-soluble or solvent-soluble metal compound), particularly a metal salt, is added to a liquid medium selected from among water, an acid aqueous solution, and a basic aqueous solution to fill the pores in the support therewith.

In an exemplary embodiment, the metal (Ni and Mo) precursors may typically be in the form of a metal salt, complex, halide, or the like. For example, the nickel precursor may be at least one selected from among nickel nitrate, nickel sulfate, nickel phosphate, nickel halide, nickel carboxylate, nickel hydroxide, nickel carbonate, acetylacetonate nickel complex, nickel acetate, hydrate thereof, and the like. More particularly, nickel nitrate and/or a hydrate thereof (e.g. Ni(NO$_3$)$_2$·6H$_2$O) may be used. Also, the molybdenum precursor that is used may be at least one selected from among molybdenum (II) acetate, ammonium (VI) molybdate, diammonium (III) dimolybdate, ammonium (VI) heptamolybdate, ammonium (VI) phosphomolybdate and similar sodium and potassium salts, molybdenum (III) bromide, molybdenum (VI) fluoride, molybdenum (III)-(V) chloride, molybdenum (VI) oxychloride, molybdenum (IV)-(VI) sulfide, molybdic acid and ammonium, sodium, and potassium salts thereof, and molybdenum (II-VI) oxide. More particularly, ammonium (VI) heptamolybdate may be used. However, the present embodiment is not limited to the nickel precursor and molybdenum precursor described above.

Meanwhile, according to the present embodiment, when the impregnation technique is used to prepare the Ni—Mo supported catalyst, it may be implemented in two ways.

Specifically, any one of nickel and molybdenum may first be supported on a support, and then the remaining metal may be supported (two-step impregnation process). For example, molybdenum may first be supported and then nickel may be supported, or vice versa.

By way of example, an impregnation solution is prepared by dissolving a precursor of nickel or molybdenum in a solvent (particularly water), and is then brought into contact with the inorganic support. Here, the concentration of the metal (Ni or Mo) precursor in the impregnation solution may be in the range of, for example, about 0.005 to 20 M, particularly about 0.01 to 10 M, and more particularly about 0.015 to 5 M. Also, the contact time may be adjusted within the range of, for example, about 0.1 to 48 hours, particularly about 0.5 to 24 hours, and more particularly about 1 to 6 hours, and the contact temperature is not particularly limited, but may be set within the range of about 1 to 100° C., particularly about 20 to 50° C., and more particularly room temperature.

After that, a drying step may be performed in an oxygen-containing atmosphere (particularly ambient air), and the drying temperature may be in the range of, for example, about 60 to 200° C., particularly about 80 to 150° C. Also, the drying time may be set within the range of, for example, about 0.5 to 15 hours, particularly about 1 to 12 hours. Through the drying process, the metal precursor may be more intimately attached to the support.

Subsequently, a firing (heat treatment) step in an oxygen-containing atmosphere (e.g. ambient air) or an inert gas atmosphere (e.g. nitrogen, etc.), particularly in an oxygen-containing atmosphere (in this case, calcination or oxidation treatment), may optionally be performed. Further, the firing (or calcination) temperature may be set within the range of, for example, about 250 to 800° C., particularly about 300 to 650° C. The firing (or calcination) time may be adjusted within the range of, for example, about 0.5 to 24 hours, particularly about 1 to 12 hours. When the firing is performed in an oxygen-containing atmosphere (i.e., calcination), the active metal may be converted into an oxide form. For example, when molybdenum is supported, it may be in a $MoO_3$ form, or when nickel is supported, it may be in a NiO form.

After the process of supporting any one of the two metals as described above, preparing an impregnation solution containing a precursor of the remaining metal and supporting the same through substantially the same method may be performed. Here, the concentration of the impregnation solution, and conditions for impregnation, drying, firing (or calcination), etc. may be set within the aforementioned ranges, and thus any detailed descriptions thereof are omitted.

Alternatively, a precursor-containing impregnation solution containing both a nickel precursor and a molybdenum precursor may be prepared and used to simultaneously support nickel and molybdenum m on an inorganic support (one-step impregnation process). In this case, when preparing the metal precursor impregnation solution, the total concentration of metal in the impregnation solution may be, for example about 0.005 to 20 M, particularly about 0.01 to 10 M, and more particularly about 0.015 to 5 M. Thereafter, subsequent steps such as impregnation of the inorganic support, drying, and firing (or calcination) may be performed in substantially the same manner as described above.

Pretreatment Process
Sulfidation Treatment

According to an embodiment, in order to pretreat the Ni—Mo supported catalyst, sulfidation treatment is first performed. Typically, sulfidation may be conducted in order to suppress aromatic loss due to excessive hydrogenation activity of active metal, or in order to impart a hydrogenation function.

According to an exemplary embodiment, the sulfidation may be performed through a method known in the art (e.g. contact with a sulfiding agent), and may broadly include a gas-phase method (contacting with hydrogen sulfide or a mixture thereof with an inert gas) or a liquid-phase method (contacting with a sulfur-compound-containing solution). According to a specific embodiment, the Ni—Mo supported catalyst may be treated with a sulfur-compound-containing solution.

According to an exemplary embodiment, the sulfiding agent or sulfur compound usable in sulfidation treatment may be at least one selected from among hydrogen sulfide, hydrogen disulfide, carbon disulfide, alkylsulfide, and the like. In particular, examples of alkylsulfide may include methylsulfide, dimethylsulfide, dimethyldisulfide, diethylsulfide, and/or dibutylsulfide. Also, the solvent that is used for the sulfidation treatment may include a hydrocarbon solvent such as benzene, toluene, xylene, C9+ aromatics, hexane, heptane, etc. Here, the concentration of the sulfur compound in the sulfidation treatment solution may be adjusted within the range of, for example, 0.001 to 50 wt %, particularly about 0.5 to 20 wt %, and more particularly about 1 to 6 wt %.

In an embodiment, the sulfur compound in the solution for the sulfidation may be appropriately used in an amount equal to or greater than the equivalent necessary to sulfide the metal in the catalyst. For example, the sulfur compound may be used in an amount equal to or greater than the equivalent necessary to sulfide the nickel in the catalyst into nickel sulfide (NiS or $Ni_3S_2$), etc., or molybdenum into $MoS_3$ (eventually capable of being converted into $MoS_2$), and may be mixed with the solution.

Through this sulfidation treatment, most of the Ni—Mo supported catalyst may be changed into $NiMoS_2$.

In an exemplary embodiment, the sulfidation treatment may be performed at a temperature ranging from room temperature to about 500° C., particularly from about 100 to 450° C., and more particularly from about 250 to 400° C. for about 0.2 to 200 hours, particularly from about 0.5 to 50 hours, and more particularly about 2 to 10 hours. Moreover, the heating rate during the sulfidation may be adjusted within the range of, for example, about 0.1 to 20° C./min, particularly about 0.3 to 10° C./min, and more particularly about 0.5 to 2° C./min. The above processing conditions are set forth merely for illustrative purposes.

Oxidation (Calcination) Treatment

According to an embodiment, the sulfided Ni—Mo catalyst as described above is subjected to oxidation (calcination) treatment. This oxidation treatment may be performed in-situ or ex-situ.

According to an exemplary embodiment, the oxidation may be performed in an oxygen-containing atmosphere, particularly in an atmosphere of oxygen alone or in an atmosphere of a mixed gas in which oxygen is diluted with an inert gas (e.g. nitrogen). The oxygen concentration in the mixed gas may be set within the range of, for example, about 0.1 to 10 vol %, particularly about 1 to 3 vol %.

Moreover, the oxidation temperature may be set to a temperature exceeding about 250° C., for example, about 300 to 700° C., specifically about 310 to 650° C., more specifically about 320 to 600° C., and even more specifically about 350 to 550° C. Here, if the oxidation treatment is performed at less than predetermined temperature, most of the catalyst remains in a sulfided form and thus the effect of decreasing the amount of unsaturated hydrocarbons in the aromatic fraction (i.e. BI reduction) after the three-step pretreatment process is almost the same as when using the catalyst subjected only to sulfidation treatment, so oxidation treatment needs to be carried out at a temperature exceeding about 250° C. On the other hand, if the oxidation temperature is too high, aromatic loss may increase due to saturation of the benzene ring in aromatics. Hence, it may be advantageous to appropriately adjust the oxidation temperature within the above range.

Moreover, the oxidation time may be adjusted within the range of, for example, about 0.2 to 300 hours, particularly about 0.5 to 150 hours, and more particularly about 1 to 24 hours. Also, the heating rate during the oxidation treatment may be adjusted within the range of, example, about 0.1 to 20° C./min, particularly about 0.3 to 10° C./min, and more particularly about 0.5 to 2° C./min. The above treatment conditions are set forth merely for illustrative purposes.

When the sulfided catalyst is subjected to oxidation treatment as described above, the catalyst is configured such that the sulfur component and the oxide are evenly distributed, and particularly, is converted into $NiS_aO_bMoS_cO_d$ ($0<(a+b)$ or $(c+d)<2$), unlike a sulfidation catalyst mainly containing $NiS$—$MoS_2$ or an oxidation catalyst having a main $NiO$—$MoO_3$ composition.

According to an exemplary embodiment, the ratio (on an atomic basis) of the amount of the metal to the amount of remaining sulfur in the oxidized catalyst may be adjusted within the range of $1.7<(Ni+Mo)/S<60$, particularly $2<(Ni+Mo)/S<50$, more particularly $3<(Ni+Mo)/S<40$, and still more particularly $4<(Ni+Mo))/S<35$. Within the above ranges, the activity of the catalyst may be increased, while aromatic loss due to hydrogenation of the benzene ring may be effectively suppressed. The above ranges are set forth merely for illustrative purposes.

Reduction Treatment

According to an embodiment, reduction treatment may be performed on the Ni—Mo catalyst subjected to sulfidation treatment and oxidation (calcination) treatment.

In an exemplary embodiment, the reduction step may be performed in a reducing atmosphere using hydrogen alone or hydrogen diluted with an inert gas (e.g. $N_2$, He, Ar, etc.). In this case, the reduction treatment may be performed at a temperature of, for example, about 25 to 650° C., particularly about 200 to 550° C., and more particularly about 300 to 500° C., and the reduction time is not particularly limited, and may be adjusted within the range of, for example, about 0.2 to 200 hours, particularly about 0.5 to 100 hours, and more particularly about 1 to 24 hours.

Through the above process, each of nickel and molybdenum may be converted in a reduced form or a partially reduced form, for example in an elemental form or a partially oxidized form. For nickel (Ni), $Ni^{2+}$ may be converted to the form of $Ni^0$, whereas for molybdenum (Mo), $Mo^{6+}$ may be converted to partially oxidized form, i.e., $Mo^{4+}$.

In particular, when the three-step pretreatment according to the present embodiment is applied to other hydrogenation catalysts, such as palladium (Pd)-based catalysts, catalysts in which nickel (Ni) alone is supported, cobalt (Co)-molybdenum (Mo) catalysts, etc., both effective BI reduction and suppression of aromatic loss cannot be realized at the same time. The pretreatment process of the present embodiment is effectively applied to the Ni—Mo catalyst (before pretreatment), thereby improving catalytic activity. Although the present disclosure is not bound by any particular theory, the metal components containing nickel and molybdenum and the sulfur component have a catalytic configuration evenly distributed in the catalyst at a predetermined ratio through the three-step pretreatment, so both the selective hydrogenation activity for unsaturated hydrocarbons and the suppression of aromatic loss, which have a tradeoff relationship therebetween, may be improved.

Selective Hydrogenation Process in Aromatic-Containing Hydrocarbon Fraction

According to another embodiment of the present disclosure, unsaturated hydrocarbons present in an aromatic-containing hydrocarbon fraction, particularly an aromatic-rich hydrocarbon fraction, are selectively hydrogenated using the Ni—Mo-based catalyst, which has been subjected to the three-step pretreatment process described above, whereby the aromatic-containing hydrocarbon fraction is purified.

In this regard, the boiling point of the aromatic-containing hydrocarbon fraction (i.e. the feedstock) may be in the range of, for example, about 35 to 300° C., particularly about 40 to 250° C., and more particularly about 50 to 220° C. According to an exemplary embodiment, the aromatic-containing hydrocarbon fraction may contain alkyl aromatic hydrocarbons. Here, the alkyl aromatic hydrocarbons may be, for example, alkyl aromatic hydrocarbons having about 6 to 18 carbon atoms, particularly about 6 to 16 carbon atoms.

The alkyl aromatic is a compound in which at least one alkyl group is attached to an aromatic ring, the alkyl group being exemplified by a methyl group, an ethyl group, a propyl group, a butyl group, etc. Specific examples thereof may include toluene, ethyltoluene, propylbenzene, tetramethylbenzene, ethyldimethylbenzene, diethylbenzene, methylpropylbenzene, ethylpropylbenzene, triethylbenzene, diisopropylbenzene, and mixtures thereof.

Also, the feedstock may further contain an aromatic compound to which an alkyl group is not attached, such as benzene, in addition to the aforementioned alkyl aromatics. In an exemplary embodiment, the feedstock may include benzene, toluene, xylene, and/or C9+ aromatics.

In the present embodiment, the aromatic-containing feedstock may contain an unsaturated hydrocarbon that increases the bromine index (BI), for example a hydrocarbon having at least one double bond and/or triple bond, including olefin, acetylene, and alkenylbenzene such as styrene (or derivatives thereof), and such unsaturated hydrocarbons are subjected to selective hydrogenation. Also, the amount of the unsaturated hydrocarbon in the aromatic-containing feedstock may be quantified by the bromine index. In the present embodiment, the bromine index of the feedstock may be in the range of, for example, at least about 30, particularly 40 to 15,000, more particularly about 50 to 10,000, and still more particularly about 100 to 8,000.

According to an exemplary embodiment, the aromatic-containing feedstock is an aromatic-rich feedstock, and the amount of the aromatic may be in the range of, for example, at least about 50 wt %, particularly at least about 70 wt %, more particularly at least about 80 wt %, and still more particularly at least about 95%. Also, the aromatic-containing feedstock may contain saturated hydrocarbons which may be contained in an amount of, for example, at most about 50 wt %, particularly at most about 30 wt %, and more particularly at most about 20 wt %.

According to an exemplary embodiment, the aromatic-containing feedstock may be obtained through, for example, catalytic reforming of naphtha; pyrolysis of naphtha, a distillate, or other hydrocarbons, which produce light olefins and aromatic-rich fractions; or catalytic cracking or thermal cracking of heavy fractions, which produce hydrocarbons in the range of the boiling point of gasoline, and these sources may be used alone or in combination as a feedstock.

According to an exemplary embodiment, the hydrogenation for removing unsaturated hydrocarbons from the aromatic-containing fraction may be carried out at a temperature ranging from room temperature to 300° C., particularly about 40 to 250° C., more particularly about 50 to 230° C., and still more particularly about 80 to 200° C.

Moreover, the hydrogenation may be performed through a liquid-phase reaction or a trickle-bed reaction using excess hydrogen. However, a liquid-phase reaction, which has a low investment cost and reduces the need to additionally separate hydrogen because the amount of hydrogen remaining after the reaction is low, may be more advantageous. The amount of hydrogen supplied thereto may be at least about 0.3 moles, particularly about 0.5 to 20 moles, and more particularly about 1 to 10 moles per mole of unsaturated hydrocarbons contained in the feedstock. If the amount of hydrogen that is supplied is excessively small or large, the removal rate of unsaturated hydrocarbons may be low, or hydrogenation of an aromatic ring may occur, causing problems of increased loss of aromatic hydrocarbons. However, the amount of hydrogen that is supplied is not limited to the above range because it may vary depending on the properties of the feedstock.

According to an exemplary embodiment, the pressure in the hydrogenation zone may be adjusted within the range of, for example, about 3 to 60 bar, particularly about 5 to 30 bar, more particularly about 7 to 20 bar, and still more particularly about 9 to 15 bar. If the pressure in the hydrogenation zone is excessively low or high, the removal rate of unsaturated hydrocarbons may be low, or hydrogenation of an aromatic ring may occur, causing problems of increased loss of aromatic hydrocarbons. Hence, it may be advantageous to appropriately adjust the pressure within the above range.

In addition, the liquid hourly space velocity (LHSV) of the aromatic-containing feedstock may be adjusted within the range of, for example, about 0.3 to 30 $hr^{-1}$, particularly about 0.5 to 20 $hr^{-1}$, and more particularly about 0.5 to 10 $hr^{-1}$.

After selective removal of the unsaturated hydrocarbons from the aromatic fraction through selective hydrogenation of the aromatic fraction containing unsaturated hydrocarbons as the feedstock, as described above, the resulting hydrogenation product may be transferred to subsequent or downstream processes, particularly the separation of benzene, toluene, and xylene products, transalkylation, xylene isomerization, and the like, thereby obtaining target compounds such as benzene, toluene, and xylenes. In this regard, the hydrogenation product contains unsaturated hydrocarbons in a decreased amount compared to the feedstock. The unsaturated hydrocarbons may be removed in an amount of at least about 30%, particularly at least about 70 wt %, more particularly at least about 80 wt %, still more particularly at least about 90%, and much more particularly at least about 95% from the feedstock through the hydrogenation. According to a specific embodiment, at least about 97%, particularly at least about 99%, and more particularly substantially all of the unsaturated hydrocarbons may be removed from the feedstock. Here, upon production of the aromatic-containing product, the aromatic loss relative to the aromatic-containing feedstock may be less than about 1 wt %, particularly less than about 0.3 wt %, and more particularly less than about 0.05 wt %.

Figure 2:
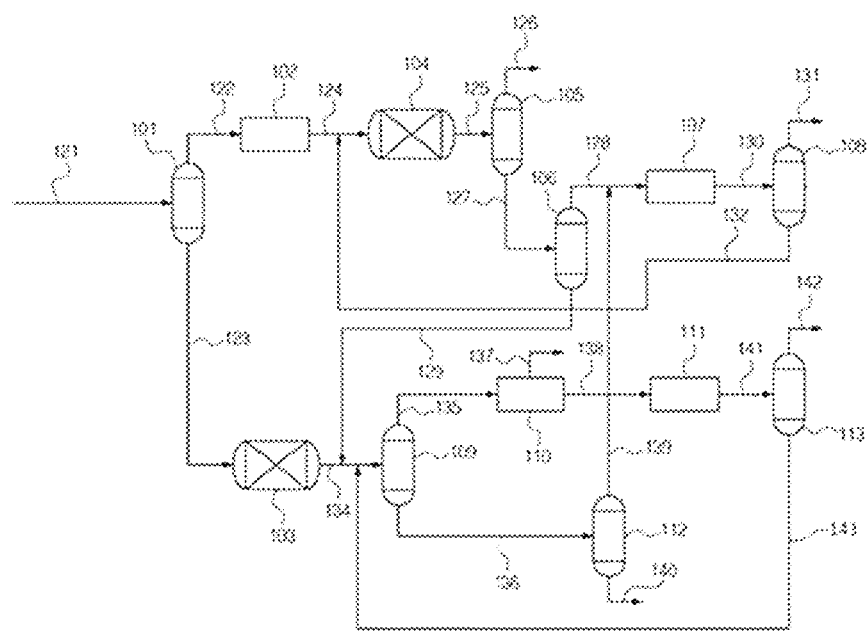
FIG. 2 schematically shows a xylene production process which comprises subjecting unsaturated hydrocarbons in an aromatic-containing feedstock to selective hydrogenation according to an exemplary embodiment.

FIG. 2 schematically shows a xylene production process 100 including selective hydrogenation of unsaturated hydrocarbons in an aromatic-containing feedstock according to an exemplary embodiment of the present disclosure.

According to the illustrated embodiment, C5+ catalytic reformate is first used as an aromatic-containing feedstock 121, and is introduced into a splitter 101. In the splitter 101, the feedstock is separated into an overhead stream including a fraction 122 containing C7− hydrocarbons (particularly C7− aromatic hydrocarbons) and a bottom stream including a fraction 123 containing C8+ hydrocarbons (particularly C8+ aromatic hydrocarbons).

As such, the fraction 122 is transferred to a benzene/toluene extraction unit 102 to obtain an extract stream 124 containing C6 and/or C7 aromatics. Here, components such as non-aromatic hydrocarbons, for example, paraffins, naphthenes, etc. may be separated as a raffinate (not shown).

The extract stream 124 may contain not only C6 and/or C7 aromatics, but also small amounts of C8+ hydrocarbons (or aromatics), and may also contain impurities that has not been completely removed during the extraction process. In addition, the extract stream may further include components other than C6 and C7 aromatics because it is combined with a fraction 132 that is recycled from a first stabilizer 108, as will be described later. In particular, unsaturated hydrocarbons to be removed in the present embodiment may be contained as impurities in the aromatic fraction 124.

With reference to FIG. 2, the fraction containing C6 and/or C7 aromatics and the recycled fraction 132 are introduced into a first hydrogenation unit 104 provided with the Ni—Mo-based catalyst pretreated as described above, thus selectively removing the unsaturated hydrocarbons therefrom. Then, a C6/C7 aromatic-containing fraction 125 from which unsaturated hydrocarbons has been reduced or removed is transferred to a benzene column 105, after which a C6 aromatic-containing fraction 126 is discharged as an overhead stream and a C7 aromatic-containing fraction 127 is discharged as a bottom stream. Here, the C6 aromatic-containing fraction 126 separated as the overhead stream may be a benzene-rich fraction, so benzene may be recovered therefrom, and, as necessary, additional purification may be performed to recover high-purity benzene.

On the other hand, the C7 aromatic-containing fraction 127 discharged as the bottom stream of the benzene column 105 is transferred to a toluene column 106, after which a C7 aromatic-rich fraction 128 and a C8+ aromatic-rich fraction 129 may be separated as an overhead stream and a bottom stream, respectively. As such, the bottom stream 129 of the toluene column 106 contains C8 aromatics (i.e. xylenes), and may thus be optionally transferred to a xylene recovery process, as will be described later. The overhead stream 128 of the toluene column 106 may be optionally introduced into a transalkylation unit 107, along with a C9 aromatic-containing stream 139, as will be described later.

The transalkylation unit 107 may involve converting the C7 aromatic-rich fraction 128 alone or in combination with the C9 aromatic-containing stream 139 into C8 aromatic hydrocarbons. Specifically, in the transalkylation unit 107, at least one of disproportionation, transalkylation, and dealkylation may be performed, for example, disproportionation of toluene, transalkylation of toluene/C9 aromatic compound, and dealkylation of alkyl aromatics, whereby C8 aromatic compounds (particularly mixed xylenes) may be produced. Since the reaction in the transalkylation unit 107 may be carried out under known reaction conditions and using known catalysts, a detailed description thereof is omitted.

A C8 aromatic-containing product stream 130 discharged after the transalkylation is introduced into the first stabilizer 108 and separated into light hydrocarbons of the transalkylation product, for example, into a C5− hydrocarbon-containing fraction 131 and a C6+ hydrocarbon (aromatic)-containing fraction 132. Here, the fraction 132 may be recycled as described above, combined with the extract stream 124 discharged from the benzene/toluene extraction unit 102, and then introduced into the first hydrogenation unit 104.

Referring again to FIG. 2, the C8+ aromatic-containing stream 123, which is the bottom stream of the splitter 101, may contain unsaturated hydrocarbons and may thus be introduced into a second hydrogenation unit 103, and unsaturated hydrocarbons are selectively removed through the hydrogenation. Here, the Ni—Mo-based catalyst pretreated as described above may be provided in the second hydrogenation unit 103. In this regard, the catalyst that is pretreated in the same manner may be applied both to the first hydrogenation unit 104 and the second hydrogenation unit 103. Alternatively, the above catalyst may be applied to any one of the first hydrogenation unit 104 and the second hydrogenation unit 103, and any other hydrogenation catalyst may be applied to the remaining reaction unit. In another exemplary embodiment, any one of the first hydrogenation unit 104 and the second hydrogenation unit 103 may be replaced with the conventional clay treatment unit, and the hydrogenation may be performed in the remaining reaction unit. In still another embodiment, a clay treatment unit may be disposed upstream or downstream of at least one of the first hydrogenation unit 104 and the second hydrogenation unit 103.

The C8+ hydrocarbon-containing fraction 134, in which the amount of the unsaturated hydrocarbons is decreased by the second hydrogenation unit 103, may be combined with the bottom stream 129 of the toluene column 106 and/or a fraction 143 that is recycled from a separator 113, as will be described later, and may then be transferred to a xylene column 109. In the xylene column 109, a xylene-rich fraction 135 as an overhead stream and a C9+ aromatic-containing stream 136 as a bottom stream are separated from each other. The xylene-rich fraction 135 thus separated is transferred to a p-xylene recovery unit 110 to selectively separate p-xylene from C8 aromatics (i.e. mixed xylene), thus selectively isolating a p-xylene-rich stream 137, from which p-xylene is then recovered. In this regard, additional separation and purification means may be further provided in order to obtain p-xylene having high purity. As the p-xylene recovery technique, Parex from UOP, Eluxyl from IFP, Aromax from Toray, etc. may be representative examples.

Most of the C8 aromatic-rich fraction 138 remaining after separation of p-xylene from the xylene recovery unit 110 may contain o-xylene and/or m-xylene. This fraction 138 may be transferred to a xylene isomerization unit 111. In this regard, in the xylene isomerization unit 111, the stream 138 containing mixed xylenes in a non-equilibrium state (a xylene mixture in which at least one C8 aromatic compound isomer is present at a concentration different from the equilibrium concentration, for example, p-xylene having a low concentration compared to an equilibrium state) is converted into xylene in the equilibrium state through isomerization. Since the reaction in the xylene isomerization unit 111 may be performed under known reaction conditions and using known catalysts, a detailed description thereof is omitted.

A product 141 discharged after the xylene isomerization is transferred to the separator 113 and separated into a C7-hydrocarbon-containing fraction 142 and a C8 aromatic-containing fraction 143. Here, the fraction 143 may be recycled and transferred to the xylene column 109 along with the fraction 134 discharged from the second hydrogenation unit 103.

On the other hand, the C9+ hydrocarbon (aromatic)-containing fraction 136, which is the bottom stream of the xylene column 109, is transferred to a C9+ column 112, after which a C9 aromatic-containing fraction 139 and a C10+ aromatic-containing fraction 140 are separated as an overhead stream and a bottom stream, respectively. As such, the C9 aromatic-containing fraction 139 may be combined with the fraction 128 and introduced into the transalkylation unit 107 described above.

A better understanding of the present invention may be obtained through the following examples, which are merely set forth to illustrate the present invention and are not construed as limiting the scope of the present invention.

EXAMPLES

The materials used in Examples and Comparative Examples are as follows.

For metal compounds and dimethyl disulfide (DMDS), ACS Reagent Grade from Sigma-Aldrich was used, and for inorganic oxides, commercially available products from Sigma-Aldrich were used. In addition, an aromatic-containing hydrocarbon fraction was obtained through a commercial process and used as a feedstock, and a C8+ aromatic fraction having a bromine index (BI) of 765 was used.

Preparation Example 1

Ni—Mo Supported/Calcined Catalyst (Ni: 5 wt %, Mo: 15 wt %)

A molybdenum precursor solution, in which ammonium heptamolybdate had been dissolved, was prepared and used to load molybdenum on an alumina support through incipient impregnation. Thereafter, the resulting support was maintained at room temperature for about 1 hour, dried at 150° C. for 2 hours in ambient air, and calcined at 500° C. for 2 hours.

Thereafter, a nickel precursor solution, in which nickel nitrate had been dissolved in distilled water, was prepared and used to additionally load nickel on the molybdenum-supported alumina support prepared as described above through incipient impregnation, followed by drying and calcining under the same conditions. Consequently, a Ni—Mo supported catalyst (Ni: 5 wt %, Mo: 15 wt %) was prepared.

Preparation Example 2

Ni—Mo Supported Dry Catalyst (Ni: 5 wt %, Mo: 15 wt %)

A molybdenum precursor solution, in which ammonium heptamolybdate had been dissolved in distilled water, was prepared and used to load molybdenum on an alumina support through incipient impregnation. Thereafter, the resulting support was maintained at room temperature for about 1 hour, and then dried at 150° C. for 2 hours in ambient air.

Thereafter, a nickel precursor solution, in which nickel nitrate had been dissolved in distilled water, was prepared and used to additionally load nickel on the molybdenum-supported alumina support prepared as described above through incipient impregnation, followed by drying under the same conditions. Consequently, a Ni—Mo dry catalyst (Ni: 5 wt %, Mo: 15 wt %) was prepared.

Preparation Example 3

NiO Supported Catalyst (Ni: 6 wt %)

A nickel precursor solution, in which nickel nitrate had been dissolved in distilled water, was prepared and used to load nickel on an alumina support through incipient impregnation. Thereafter, the resulting support was maintained at room temperature for about 1 hour, dried at 150° C. for 2 hours in ambient air, and then calcined at 500° C. for 2 hours. Here, the heating rate was adjusted to 3° C./min. Consequently, a NiO/alumina catalyst having Ni content of 6 wt % was prepared.

Preparation Example 4

Co—Mo Supported Catalyst (Co: 5 wt %, Mo: 15 wt %)

A Co—Mo supported catalyst (Co: 5 wt %, Mo: 15 wt %) was prepared according to the same procedure as in Preparation Example 1, with the exception that cobalt nitrate was used as a cobalt precursor instead of the nickel precursor.

Preparation 5

Ni—Cu Supported Catalyst (Ni: 30 wt %, Cu: 0.5 wt %)

Nickel chloride and copper chloride were dissolved in distilled water and mixed with a pseudoboehmite powder as an alumina precursor to prepare a paste, which was then shaped (molded) using an extrusion molding machine equipped with a round die having a diameter of 1.6 mm. Thereafter, the shaped product was maintained at room temperature for about 1 hour, dried at 150° C. for 2 hours in ambient air, and calcined at 500° C. for 2 hours. Here, the heating rate was adjusted to 3° C./min. Consequently, a NiO—CuO/alumina catalyst having Ni content of 30 wt % and Cu content of 0.5 wt % was prepared.

Example 1

Three-Step Pretreatment Including Sulfidation, In-Situ Oxidation, and Reduction of Calcined Ni—Mo Supported Catalyst 40 cc of the Ni—Mo supported catalyst prepared according to Preparation Example 1 (catalyst size distribution: 20 to 40 mesh) was charged in a continuous fixed-bed reactor. Subsequently, after the atmosphere in the reactor was purged with nitrogen, the pressure thereof was increased to 9 kgf/cm$^2$. Thereafter, nitrogen was replaced with hydrogen, and toluene mixed with 4 wt % DMDS was injected at 0.7 cc/min while allowing hydrogen to flow at 500 cc/min. After maintaining for 5 hours, the temperature was elevated to 350° C. at a heating rate of 1° C./min, and sulfidation was performed for 3 hours.

Thereafter, injection of the toluene solution mixed with DMDS was stopped, the temperature was lowered to 200° C., $H_2$ was replaced with $N_2$, and $N_2$ was allowed to flow at 1000 cc/min to remove $H_2$, after which $N_2$ containing 2% $O_2$ was injected at 1000 cc/min, the temperature was elevated to 400° C. at a heating rate of 1° C./min and maintained for 12 hours, and oxidation was performed.

$N_2$ containing 2% $O_2$ was replaced again with $N_2$, and $N_2$ was allowed to flow at 1000 cc/min to remove $O_2$, after which the temperature was lowered to 100° C. at a cooling rate of 1° C./min. When the temperature of the reactor was stabilized, $N_2$ was replaced with $H_2$, $H_2$ was allowed to flow at 1000 cc/min, and the temperature was elevated to 400° C. at a heating rate of 1° C./min, followed by reduction for 2 hours.

Example 2

Three-Step Pretreatment Including Sulfidation, Ex-Situ Oxidation, and Reduction of Calcined Ni—Mo Supported Catalyst 40 cc of the Ni—Mo supported catalyst prepared according to Preparation Example 1 (catalyst size distribution: 20 to 40 mesh) was charged in a continuous fixed-bed reactor. Then, after the atmosphere in the reactor was purged with nitrogen, the pressure thereof was increased to 9 kgf/cm$^2$. Thereafter, nitrogen was replaced with hydrogen, and toluene mixed with 4 wt % DMDS was injected at 0.7 cc/min while allowing hydrogen to flow at 500 cc/min. After maintaining for 5 hours, the temperature was elevated to 350° C. at a heating rate of 1° C./min, and sulfidation was performed for 3 hours.

Thereafter, the temperature was lowered to 200° C., injection of the toluene solution mixed with DMDS was stopped, $H_2$ was replaced with $N_2$, and $N_2$ was allowed to flow at 1000 cc/min to remove $H_2$, after which the temperature was lowered to room temperature. Next, the sulfided catalyst was taken out of the reactor and placed in a calcination furnace, and the temperature was elevated to 400° C. at a heating rate of 1° C./min, maintained for 3 hours, and then lowered to room temperature.

The catalyst that was oxidized after sulfidation was charged again in the reactor, air was replaced with nitrogen at 1000 cc/min, and nitrogen was replaced with hydrogen, after which hydrogen was allowed to flow at 1000 cc/min. Thereafter, the temperature was elevated to 400° C. at a heating rate of 1° C./min, followed by reduction for 2 hours.

Example 3

Three-Step Pretreatment Including Sulfidation, Ex-Situ Oxidation, and Reduction of Dry Ni—Mo Catalyst Pretreatment was performed in the same manner as in Example 2, with the exception that the dry Ni—Mo catalyst prepared according to Preparation Example 2 was used.

Comparative Example 1

Sulfidation Pretreatment of Calcined Ni—Mo Supported Catalyst 40 cc of the Ni—Mo supported catalyst prepared according to Preparation Example 1 (catalyst size distribution: 20 to 40 mesh) was charged in a continuous fixed-bed reactor. Next, after the atmosphere in the reactor was purged with nitrogen, the pressure thereof was increased to 9 kgf/cm$^2$. Thereafter, nitrogen was replaced with hydrogen, and toluene mixed with 4 wt % DMDS was injected at 7 cc/min while allowing hydrogen to flow at 500 cc/min. After maintaining for 5 hours, the temperature was elevated to 350° C., and sulfidation was performed for 3 hours.

Comparative Example 2

Reduction Pretreatment of Calcined Ni—Mo Supported Catalyst 40 cc of the Ni—Mo supported catalyst prepared according to Preparation Example 1 (catalyst size distribution: 20 to 40 mesh) was charged in a continuous fixed-bed reactor. Subsequently, after the atmosphere in the reactor was purged with nitrogen, the pressure thereof was increased to 9 kgf/cm$^2$. Thereafter, nitrogen was replaced with hydrogen, and the temperature was elevated to 400° C. while allowing hydrogen to flow at 1000 cc/min, followed by reduction for 2 hours.

Comparative Example 3

Reduction-Sulfidation Pretreatment of Calcined Ni—Mo Supported Catalyst 40 cc of the calcined Ni—Mo supported catalyst prepared according to Preparation Example 1 (catalyst size distribution: 20 to 40 mesh) was charged in a continuous fixed-bed reactor. Next, after the atmosphere in the reactor was purged with nitrogen, the pressure thereof was increased to 9 kgf/cm². Thereafter, nitrogen was replaced with hydrogen, and the temperature was elevated to 400° C. while allowing hydrogen to flow at 1000 cc/min, followed by reduction for 2 hours.

Thereafter, the temperature of the reactor was lowered to 150° C., after which 0.7 cc/min of toluene mixed with 4 wt % DMDS and 1000 cc/min of hydrogen were allowed to flow, and after maintaining for 5 hours the temperature was elevated to 350° C., followed by sulfidation for 3 hours.

Comparative Example 4

Reduction Pretreatment of NiO Supported Catalyst (Ni: 6 wt %)

40 cc of the NiO supported catalyst prepared according to Preparation Example 3 (catalyst size distribution: 20 to 40 mesh) was charged in a continuous fixed-bed reactor. Subsequently, after the atmosphere in the reactor was purged with nitrogen, the pressure thereof was increased to 9 kgf/cm². Thereafter, nitrogen was replaced with hydrogen, and the temperature was elevated to 400° C. while allowing hydrogen to flow at 1000 cc/min, followed by reduction for 2 hours.

Comparative Example 5

Reduction Pretreatment of Pd Supported Catalyst (Pd: 6 wt %)

A palladium precursor solution in which palladium chloride was dissolved in distilled water was prepared and used to load palladium on an alumina support through incipient impregnation. Thereafter, the resulting palladium precursor-loaded support was maintained at room temperature for about 1 hour, dried at 150° C. for 2 hours in ambient air, and calcined at 500° C. for 2 hours. As such, the heating rate was adjusted to 3° C./min. Consequently, a PdO/alumina catalyst having Pd content of 6 wt % was prepared.

40 cc of the PdO/alumina catalyst prepared as described above (catalyst size distribution: 20 to 40 mesh) was charged in a continuous fixed-bed reactor. Subsequently, after the atmosphere in the reactor was purged with nitrogen, the pressure thereof was increased to 9 kgf/cm². Thereafter, nitrogen was replaced with hydrogen, and the temperature was elevated to 400° C. while allowing hydrogen to flow at 1000 cc/min, followed by reduction for 2 hours.

Comparative Example 6

Sulfidation Pretreatment of Calcined Co—Mo Supported Catalyst 40 cc of the calcined Co—Mo supported catalyst prepared according to Preparation Example 4 (catalyst size distribution: 20 to 40 mesh) was charged in a continuous fixed-bed reactor. Next, after the atmosphere in the reactor was purged with nitrogen, the pressure thereof was increased to 9 kgf/cm². Thereafter, nitrogen was replaced with hydrogen, and toluene mixed with 4 wt % DMDS was injected at 0.7 cc/min while allowing hydrogen to flow at 500 cc/min. After maintaining for 5 hours, the temperature was elevated to 350° C., and sulfidation was performed for 3 hours.

Comparative Example 7

Three-Step Pretreatment Including Sulfidation, In-Situ Oxidation, and Reduction of Calcined Co—Mo Supported Catalyst Pretreatment was carried out in the same manner as in Example 1, with the exception that the Co—Mo supported catalyst prepared according to Preparation Example 4 was used, and a reaction experiment was performed.

Comparative Example 8

Three-Step Pretreatment Including Sulfidation, In-Situ Oxidation, and Reduction of Ni—Cu Catalyst Pretreatment was carried out in the same manner as in Example 1, with the exception that the Ni—Cu supported catalyst prepared according to Preparation Example 5 was used, and a reaction experiment was performed.

Test Example 1

The temperature of the reactor packed with the catalyst prepared according to each of Examples 1 to 3 and Comparative Examples 1 to 8 was adjusted to 150° C., after which the flow rate of $H_2$ was adjusted to 12 cc/min, and a hydrogenation reaction was carried out (reaction pressure: 9 bar) while allowing a C8+ aromatic fraction (BI: 765, aromatic content: 99 wt %) to flow at 1.5 cc/min. After reaction for 24 hours, the reaction product was sampled, followed by BI measurement and gas chromatography, and the BI value and aromatic loss were calculated, and the results thereof are shown in Table 1 below (in which ①, ②, and ③ are the sequence of pretreatment processes).

TABLE 1

| Classification | Metal | Sulfidation | Oxidation (° C.) | Reduction | Metal/S weight ratio[1] | BI | Aromatic loss (wt %) | Remark |
|---|---|---|---|---|---|---|---|---|
| Example 1 | NiMo | ① | ② (400) In-situ | ③ | 7.6 | 25 | 0.03 | Excellent unsaturated hydrocarbon removal performance, almost no aromatic loss |
| Example 2 | NiMo | ① | ② (400) Ex-situ | ③ | 8.3 | 28 | 0.03 | Excellent unsaturated hydrocarbon removal performance, almost no aromatic loss |
| Example 3 | NiMo | ① | ② (400) Ex-situ | ③ | 9.2 | 30 | 0.03 | Excellent unsaturated hydrocarbon removal performance, almost no aromatic loss |

TABLE 1-continued

| Classification | Metal | Sulfidation | Oxidation (° C.) | Reduction | Metal/S weight ratio[1] | BI | Aromatic loss (wt %) | Remark |
|---|---|---|---|---|---|---|---|---|
| Comparative Example 1 | NiMo | ① | | | 1.3 | 172 | 0.02 | Very low unsaturated hydrocarbon removal performance |
| Comparative Example 2 | NiMo | | | ① | — | 49 | 0.85 | High aromatic loss |
| Comparative Example 3 | NiMo | | ② | | — | 200 | 0.02 | Very low unsaturated hydrocarbon removal performance |
| Comparative Example 4 | Ni | | | ① | — | 51 | 1.32 | High aromatic loss |
| Comparative Example 5 | Pd | | | ① | — | 54 | 0.35 | High aromatic loss |
| Comparative Example 6 | CoMo | ① | | | | 172 | 0.02 | Very low unsaturated hydrocarbon removal performance |
| Comparative Example 7 | CoMo | ① | ② (400) In-situ | ③ | — | 202 | 0.02 | Very low unsaturated hydrocarbon removal performance |
| Comparative Example 8 | NiCu | ① | ② (400) In-situ | ③ | 10 | 29 | 3.4 | High aromatic loss |

[1]Weight ratio of metal (Ni + Mo)/S remaining in catalyst after oxidation treatment As shown in Table 1, the catalysts (NiMo) according to Examples 1 to 3, in which three-step pretreatment was performed, were vastly superior in unsaturated hydrocarbon removal performance compared to the catalyst (NiMo) of Comparative Example 1, in which only sulfidation pretreatment was performed, and aromatic loss was at a similar level. Furthermore, when compared with the catalyst (NiMo) of Comparative Example 2, in which only reduction pretreatment was performed, unsaturated hydrocarbon removal performance was excellent, and aromatic loss was also comparatively very low. In addition, when compared with the catalysts used in similar commercial processes, unsaturated hydrocarbon removal performance was excellent. In particular, aromatic loss was very low compared to the Ni catalyst, the Pd catalyst, and the Ni—Cu catalyst.

Examples 4 and 5 and Comparative Examples 9 and 10

Pretreatment was performed in the same manner as in Example 2, with the exception that the calcination temperature was changed to 350° C., 550° C., 700° C., and 250° C. in the oxidation step.

Test Example 2

This test example was performed in the same manner as in Test Example 1 using the catalyst of each of Examples 2, 4, and 5 and Comparative Examples 9 and 10, and the results thereof are shown in Table 2 below (in which ①, ②, and ③ are the sequence of pretreatment processes).

TABLE 2

| Classification | Metal | Sulfidation | Oxidation (° C.) | Reduction | Metal/S weight ratio | BI | Aromatic loss (wt %) | Remark |
|---|---|---|---|---|---|---|---|---|
| Example 2 | NiMo | ① | ② (400) Ex-situ | ③ | 8.3 | 28 | 0.03 | Excellent unsaturated hydrocarbon removal performance, almost no aromatic loss |
| Example 4 | NiMo | ① | ② (350) Ex-situ | ③ | 4.3 | 35 | 0.03 | Excellent unsaturated hydrocarbon removal performance, almost no aromatic loss |
| Example 5 | NiMo | ① | ② (550) Ex-situ | ③ | 32.3 | 25 | 0.03 | Excellent unsaturated hydrocarbon removal performance, almost no aromatic loss |
| Comparative Example 9 | NiMo | ① | ② (700) Ex-situ | ③ | 60 | 114 | 0.56 | Low unsaturated hydrocarbon removal performance, some aromatic loss |

TABLE 2-continued

| Classification | Metal | Sulfidation | Oxidation (° C.) | Reduction | Metal/S weight ratio | BI | Aromatic loss (wt %) | Remark |
|---|---|---|---|---|---|---|---|---|
| Comparative Example 10 | NiMo | ① | ② (250) Ex-situ | ③ | 1.5 | 142 | 0.02 | Low unsaturated hydrocarbon removal performance |

As shown in Table 2, differences in unsaturated hydrocarbon removal performance and aromatic loss were observed depending on changes in the oxidation temperature during the three-step pretreatment. In particular, in the catalyst at an oxidation temperature of 250° C. (Comparative Example 10), unsaturated hydrocarbon removal performance was low, similar to that of the catalyst according to Comparative Example 1, in which only sulfidation was performed. Also, in the catalyst calcined at 700° C. (Comparative Example 9), unsaturated hydrocarbon removal performance was deteriorated and aromatic loss was greatly increased.

In particular, based on the results of analysis of the components of the catalyst at different oxidation temperatures, the weight ratio of metal/sulfur was increased in proportion to the increase in the calcination temperature. Moreover, when the weight ratio of metal/sulfur was 60 (Comparative Example 9), aromatic loss was increased.

As is apparent from the above description, a bimetallic nickel-molybdenum catalyst having relatively high hydrogenation activity but a tendency to cause aromatic loss by hydrogenating even the benzene ring of an aromatic fraction (particularly, single benzene-ring aromatic hydrocarbons) due to excessive hydrogenation is subjected to pretreatment three-step of sulfidation, oxidation (calcination), and reduction, thereby effectively removing unsaturated hydrocarbons from the aromatic fraction, and simultaneously suppressing aromatic loss, and maintaining good selective hydrogenation activity even upon long-term operation.

Simple modifications or variations of the present invention can be easily devised by those of ordinary skill in the art, and all such modifications or variations can be considered to be included in the scope of the present invention.

The invention claimed is:

1. A method for removing unsaturated hydrocarbons from aromatic hydrocarbons, which comprises the steps of:
   providing an aromatic hydrocarbon-containing feedstock having a bromine index of at least 30; and
   forming an aromatic hydrocarbon-containing product having a decreased bromine index compared to the feedstock by hydrogenating the aromatic hydrocarbon-containing feedstock in presence of a selective hydrogenation catalyst prepared using a method comprising the steps of:
   a) providing a calcined catalyst containing nickel and molybdenum;
   b) sulfiding the calcined catalyst containing nickel and molybdenum to give a sulfided catalyst containing nickel and molybdenum;
   c) carrying out an oxidation treatment of the sulfided catalyst containing nickel and molybdenum at a temperature exceeding 250° C. to give an oxidized catalyst containing nickel and molybdenum; and
   d) carrying out a reduction treatment of the oxidized catalyst containing nickel and molybdenum to give a reduced catalyst containing nickel and molybdenum.

2. The method of claim 1, wherein at least 30 wt % of an unsaturated hydrocarbon is removed from the aromatic hydrocarbon-containing feedstock, and aromatic loss upon production of the aromatic hydrocarbon-containing product from the aromatic hydrocarbon-containing feedstock is less than 1 wt %.

3. The method of claim 1, wherein an amount of hydrogen that is supplied in the hydrogenating is at least 0.3 moles per mole of the unsaturated hydrocarbon contained in the feedstock.

4. The method of claim 1, wherein a temperature of the hydrogenating is set within a range from room temperature to 300° C., and a pressure of the hydrogenating is set within a range of 3 to 60 bar.

5. The method of claim 1, further comprising:
   separating at least one aromatic hydrocarbon selected from the group consisting of C6 aromatics, C7 aromatics, C8 aromatics, and C9+ aromatics from the aromatic hydrocarbon-containing product; and
   forming a C8 aromatic hydrocarbon-containing product by converting a fraction comprising C6 aromatic hydrocarbon, C7 aromatic hydrocarbon, and/or C9+ aromatic hydrocarbons in the separated aromatic hydrocarbon-containing product into C8 aromatic hydrocarbons through a transalkylation reaction.

6. The method of claim 5, further comprising separating and recovering para-xylene from the C8 aromatic hydrocarbon-containing product and forming a C8 aromatic hydrocarbon fraction having increased para-xylene content by isomerizing an unrecovered C8 aromatic hydrocarbons.

7. The method of claim 1, wherein the calcined catalyst containing nickel and molybdenum is a catalyst in which nickel and molybdenum are loaded on an inorganic support, an amount of nickel being 1 to 30 wt % and an amount of molybdenum being 2 to 40 wt %.

8. The method of claim 1, wherein step c) is performed at a temperature of 300 to 700° C.

9. The method of claim 1, wherein a weight ratio of metal (nickel and molybdenum)/sulfur in the oxidized catalyst containing nickel and molybdenum in step c) is greater than 1.7 and less than 60.

10. The method of claim 7, wherein an atomic ratio of nickel to molybdenum in the calcined catalyst containing nickel and molybdenum is 1:0.1 to 10.

11. The method of claim 7, wherein the inorganic support is at least one selected from the group consisting of alumina, silica, silica-alumina, aluminum phosphate, zirconia, titania, bentonite, kaolin, clinoptilolite, and montmorillonite.

12. The method of claim 1, wherein step a) comprises:
   a1) depositing a nickel precursor and a molybdenum precursor on an inorganic support simultaneously or sequentially to give a nickel-molybdenum deposited support; and
   a2) firing the nickel-molybdenum deposited support in an oxygen-containing atmosphere to give the calcined catalyst containing nickel and molybdenum.

13. The method of claim 1, wherein step b) is performed at a temperature ranging from room temperature to 500° C. for 0.2 to 200 hours using, as a sulfiding agent, at least one sulfur compound selected from the group consisting of hydrogen sulfide, hydrogen disulfide, carbon disulfide, and alkyl sulfide.

14. The method of claim 13, wherein step b) is performed using a sulfidation treatment solution in which the at least one sulfur compound is added to a hydrocarbon-based solvent, a concentration of the at least one sulfur compound in the sulfidation treatment solution being 0.001 to 50 wt %.

15. The method of claim 1, wherein step c) is performed for 0.2 to 300 hours in an atmosphere of oxygen alone or in an atmosphere of a mixed gas in which oxygen is diluted with an inert gas, a heating rate being adjusted within a range of 0.1 to 20° C./min.

16. The method of claim 1, wherein step d) is performed at 25 to 650° C. for 0.2 to 200 hours in a reducing atmosphere using hydrogen alone or hydrogen diluted with an inert gas.

17. The method of claim 7, wherein the inorganic support has an average pore diameter in a range of 3 to 1000 nm, and a specific surface area (BET) in a range of 10 to 1000 m2/g.

18. The method of claim 12, wherein the nickel precursor is selected from the group consisting of nickel nitrate, nickel sulfate, nickel phosphate, nickel halide, nickel carboxylate, nickel hydroxide, nickel carbonate, acetylacetonate nickel complex, nickel acetate, and hydrate thereof, and the molybdenum precursor is selected from the group consisting of molybdenum (II) acetate, ammonium (VI) molybdate, diammonium (III) dimolybdate, ammonium (VI) heptamolybdate, ammonium (VI) phosphomolybdate and similar sodium and potassium salts, molybdenum (III) bromide, molybdenum (III)-(V) chloride, molybdenum (VI) fluoride, molybdenum (VI) oxychloride, molybdenum (IV)-(VI) sulfide, molybdic acid and ammonium, sodium, and potassium salts thereof, and molybdenum (II-VI) oxide.

19. The method of claim 1, wherein the nickel in the sulfided catalyst is converted into NiS and/or Ni3S2, while the molybdenum in the sulfided catalyst is converted into MoS3.

20. The method of claim 19, wherein the oxidized catalyst has a formula of $NiS_aO_bMoS_cO_d$ (0<(a+b) or (c+d)<2).

* * * * *